Figure 1:
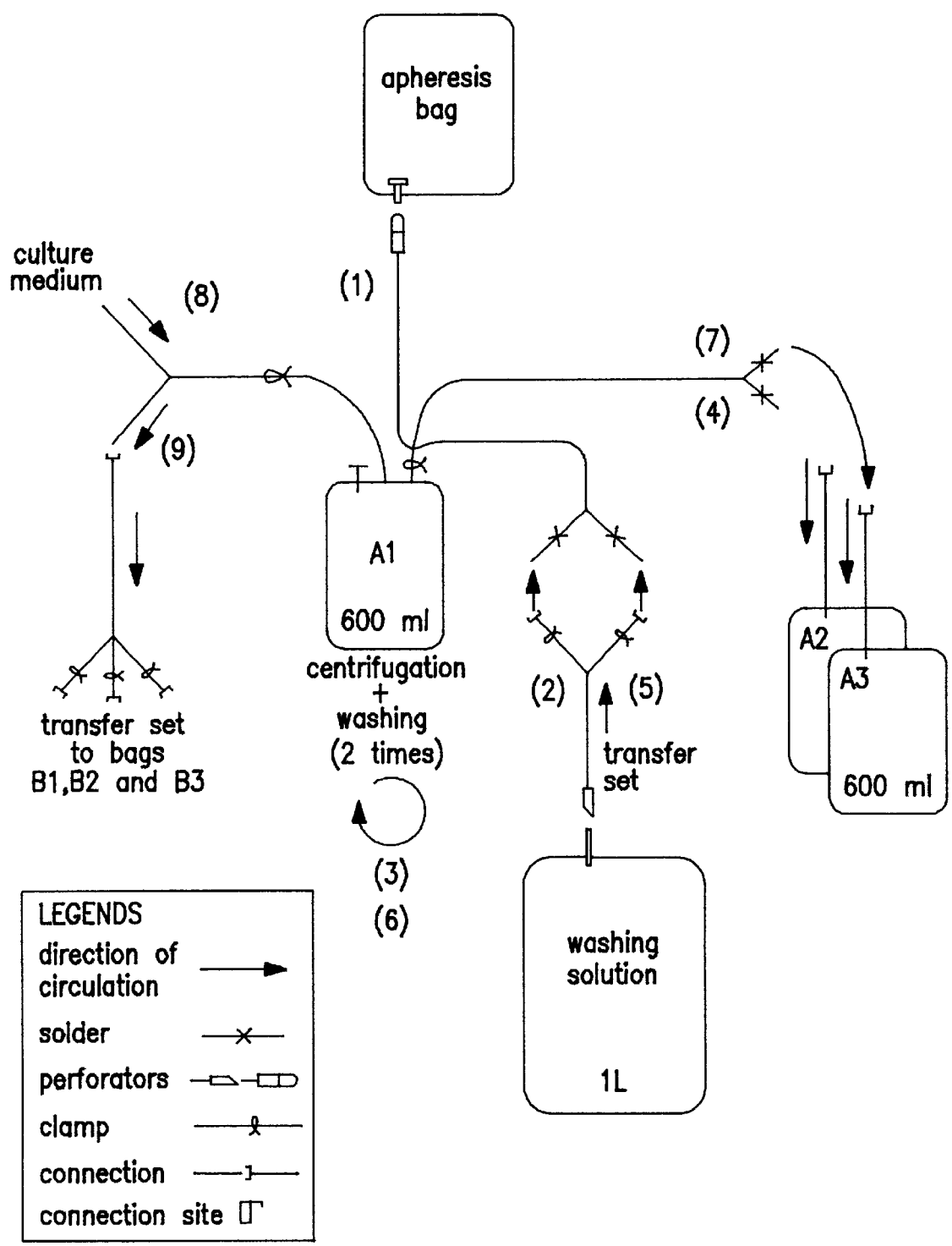

United States Patent [19]
Romet-Lemonne et al.

[11] Patent Number: 6,140,122
[45] Date of Patent: Oct. 31, 2000

[54] PROCESS FOR PREPARING MACROPHAGES, KITS, AND COMPOSITIONS FOR THE USE OF THIS PROCESS

[75] Inventors: Jean-Loup Romet-Lemonne, Paris; Mohamed Chokri, Deuil-la-Barre, both of France

[73] Assignee: I.D.M. Immuno-Designed Molecules, Paris, France

[21] Appl. No.: 09/025,454

[22] Filed: Feb. 18, 1998

Related U.S. Application Data

[60] Division of application No. 08/654,383, May 28, 1996, Pat. No. 5,804,442, which is a continuation-in-part of application No. PCT/FR96/00121, Jan. 24, 1996.

[30] Foreign Application Priority Data

Jan. 24, 1995 [FR] France .................................. 95 00785

[51] Int. Cl.$^7$ ...................................................... C12N 5/00
[52] U.S. Cl. .......................... 435/374; 435/372; 435/405; 435/975
[58] Field of Search ..................................... 435/374, 405, 435/372, 975

[56] References Cited

FOREIGN PATENT DOCUMENTS

WO 94/26875  11/1994  WIPO .

OTHER PUBLICATIONS

Chokri, M. et al., "Production of Human Macrophages with Potent Antitumor Properties (MAK) by Culture of Monocytes in the Presence of GM–CSF and 1.25–Dihydroxy vitamin D3", *Anticancer Research*, vol. 12, No. 6B, pp2257–2260. .

Faradji, A. et al., "Apheresis–Elutriation Program for Adoptive Immunotherapy with Autologous Activated Monocytes in Cancer Patients", *The International Journal of Artificial Organs*, vol. 14, No. 5, 1991, pp. 304–312.

Lopez, M. et al., "Autologous Lymphocytes Prevent the Death of Monocytes in Culture and Promote as DO GM–CSF IL–3 and M–CSF Their Differentiation into Macrophages", *Journal of Immunological Methods*, vol. 159, No. 1–2, 1993, pp. 29–38.

E. Helsinki et al., "Tumor–Cytolytic Human Macrophages Cultured As Nonadherent Cells: Potential for the Adoptive Immunotherapy of Cancer", *Cancer Detection and Prevention*, 1990, pp. 471–481.

R. Andreesen et al., "Primary Cultures of Human Blood–Born Macrophages Grown on Hydrophobic Teflon Membranes", *Journal of Immunological Methods*, vol. 56, 1983, pp. 295–304.

R. Andreesen et al., "Activation of Human Monocyte–Derived Macrophages Cultured on Teflon: Response to Interferon–y during Terminal Maturation in vitro", *Immunobiol.*, vol. 177, 1988, pp. 186–198.

*Primary Examiner*—Leon B. Lankford, Jr.
*Attorney, Agent, or Firm*—Young & Thompson

[57] ABSTRACT

The invention relates to a process for preparing a composition comprising macrophages, optionally activated, and/or cells derived from monocytes with a strong potential for antigen presentation, said process comprising a stage of culture of monocytes present in the starting composition, this stage being preceding and/or followed by a stage of elimination of all or part of the constituents other than the monocytes present in the starting composition, with the aid of antibodies directed against said constituents, and/or followed by a stage of elutriation. The invention also concerns the compositions of kits for reducing this process to practice.

21 Claims, 3 Drawing Sheets

PROCESS FOR PREPARING MACROPHAGES, KITS, AND COMPOSITIONS FOR THE USE OF THIS PROCESS

CROSS-REFERENCE TO RELATED APPLICATIONS

This application is a division of application Ser. No. 08/654,383, filed May 28, 1996, now U.S. Pat. No. 5,804,442 and a continuation-in-part of PCT/FR96/00121.

The present invention relates to a process for preparing macrophages, specifically human macrophages, in particular activated macrophages (also designated as cytotoxic macrophages) or macrophages (or other cells derived from monocytes or from their precursors) for the presentation of antigens, as well as kits and compositions which may be used for this process.

Macrophages play a major role in the antitumoral response, and they are able to be activated by immunological activators against cancer cells (Adams D. and Hamilton T.: Activation of macrophages for tumor cell kill: effector mechanism and regulation. In Heppner & Fulton (eds), Macrophages and cancer. CRC Press, 1988, p. 27; Fidler I.: Macrophages and metastases. A biological approach to cancer therapy. Cancer Res. 45: 4714, 1985).

Furthermore, macrophages, or other cells derived from monocytes or from their precursors, with their strong capacity for endocytosis, digestion, and surface antigen presentation, are capable of inducing a specific immune response. In this way, they represent good candidates for the preparation of vaccines, and more specifically cellular autologous vaccines. Macrophages, or other cells derived from monocytes, presenting antigens on their surface specifically capable of inducing a specific immune response, are designated in the text which follows as MD-APCs (Monocyte-Derived Antigen Presenting Cells).

The MD-APCs are obtained by culture of mononucleated cells (monocytes or their precursors), taken from a patient or healthy individual, in the presence of one (or several) antigen(s) which are desired to be expressed as fragments on the surface of the cells obtained at the end of the culture period.

The antigens which may be cultured with the above mentioned mononucleated cells are, for example, antigens expressed by tumor cells (in particular fragments of killed tumor cells) or by pathogens (in particular bacterial or viral protein fragments).

The MD-APCs thus obtained are used for the preparation of vaccines directed against the pathology associated with the antigen co-cultivated with the mononucleated cells (in particular vaccines against tumors or viral diseases) and more particularly for the preparation of autologous cellular vaccines which are advantageously administered to the patient from whom the starting mononucleated cells were taken.

MD-APCs are also able to be obtained by transfection of the above mentioned cells placed in culture, or of differentiated cells, in particular macrophages, obtained after culture, with DNA sequences coding for antigen fragments such as those defined above.

Macrophages presenting cytotoxic activity which is particularly significant (also designated as activated macrophages or MAK (registered trade mark)) as well as a culture medium and process for obtaining said macrophages were the subject matter of international patent application no. PCT/EP 93/01232, filed on May 18, 1993.

The process for preparing macrophages defined in the above mentioned international patent application is carried out with a composition rich in blood cells obtained by apheresis from a healthy individual, and includes a stage of monocyte culture in a culture medium containing vitamin D3 1.25-dihydroxyl and GM-CSF (Granulocyte-Macrophage colony stimulating factor). Advantageously, the monocytes are cultivated in the presence of lymphocytes for about 6 to 7 days, and the differentiated macrophages thus obtained are activated in the culture medium by the addition of interferon γ (IFN-γ).

This culture stage is preceded, as in all procedures for obtaining macrophages described up to today, by a stage of separation of, in one part, mononuclear cells, and, in another part, red cells, granulocytes, and part of the platelets contained in the composition derived from blood obtained by apheresis; and by a stage of elimination, by washing part of the blood platelets and anticoagulants remaining after the preceding separation stage.

The above mentioned stage of separation of red cells and granulocytes is generally carried out by centrifugation of the medium containing the monocytes on a density gradient, particularly in a solution having a specific weight of about 1.0 to about 1.3 g/ml, such as Ficoll Paque solution (Pharmacia) with a specific weight of 1.077 g/ml.

In the above mentioned international patent application, the composition derived from the blood is obtained by apheresis containing approximately 7 to $9 \times 10^9$ leukocytes in a volume of approximately 200 ml. After the stage of separation of the red cells and granulocytes by centrifugation on a density gradient, the composition of cellular suspension placed in culture thus contains, in a volume of approximately 500 ml to 1000 ml:

| | |
|---|---|
| Hematocrit (Red cells) | <0.1% of the number of the white cells present in the composition |
| Platelets | $<10^{10}$ |
| White cells | $3$ to $5 \times 10^9$ |
| Lymphocytes | 50–70% of the number of white cells present in the composition |
| Monocytes | 30–50% of the number of white cells present in the composition |
| Polynuclear cells (or granulocytes) | <5% of the number of white cells present in the composition |

The elimination of red cells and granulocytes, which is done beforehand in the culture stage, has always been considered as an indispensable stage, due particularly to the fact that the granulocytes are liable to totally or partially inhibit the differentiation of monocytes into macrophages during the culture stage.

This inhibition would principally be due to the fact that red cells, granulocytes and platelets use the constituents of the culture medium for their own metabolism, thus exhausting the reserves necessary for the development of the monocytes, and leading to acidification of the culture medium in proportions such that the culture stage cannot be completed (usually requiring about 6 to 7 days).

Furthermore, the granulocytes and platelets would be particularly liable to secrete suppresser factors, such as TGF (transforming growth factor), and prostaglandins, against the functionality of macrophages.

Therefore, it is currently acknowledged that the granulocytes and as many of the platelets as possible should be separated from the monocytes before being placed in culture with the latter, even though this separation leads to the elimination of about 20% to about 50%, in particular about 30%, of the mononucleated cells present in the medium before separation.

The present invention aims at providing a new process for obtaining macrophages or MD-APCs, optionally activated, which is the most simple procedure described up to today and presents the best results of all the processes for obtaining macrophages described up to today.

The invention also aims at providing kits (or cases) for carrying out this process.

The invention also aims at providing for the user of said kits, compositions which can be used as internal controls in order to control the different stages of the process, particularly to control the contents of monocytes, and optionally of other constituents of the starting composition of the process of the invention, and to control the contents of macrophages or MD-APCs, optionally activated, in the final composition being sought.

Figure 2:
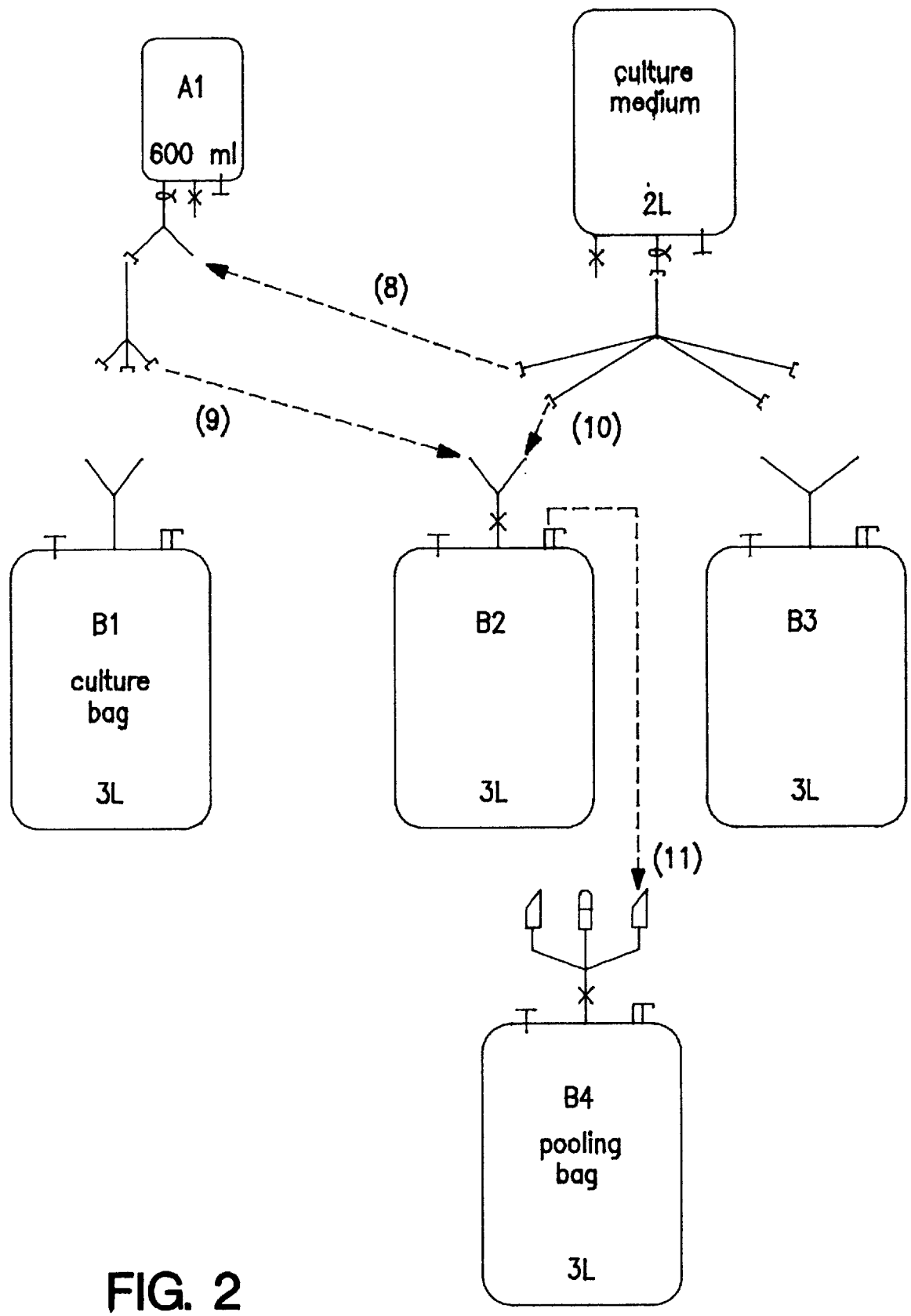
Figure 3:
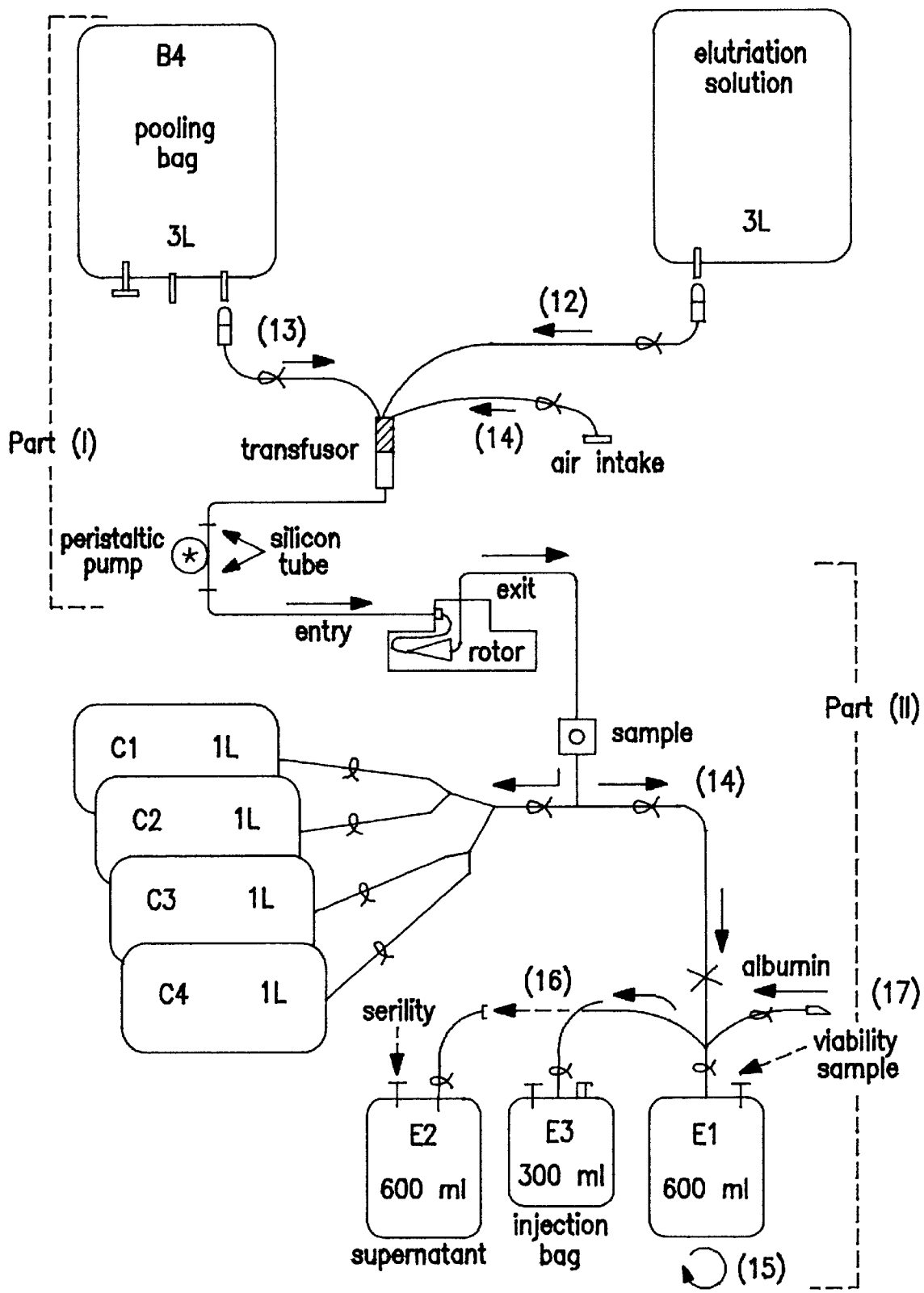

The present invention is illustrated with the aid of the following figures:

FIG. 1 represents the assembly for the removal of platelets and washing the product of apheresis, FIG. 2 represents the assembly of the culture of mononucleated cells for obtaining macrophages or MD-APCs, FIG. 3 represents the assembly of the elutriation system.

The present invention relates to a process for obtaining macrophages and MD-APCs, optionally activated, not including a stage of separation by physical means, notably by centrifugation on a density gradient in the way described above, in one part, of the red cells and/or granulocytes, and, in another part, of other white cells, notably monocytes, present in the composition derived from blood and obtained by apheresis.

The invention particularly relates to any process for preparing a composition containing macrophages or MD-APCs, optionally activated, characterized in that, starting from a composition derived from blood of human origin, rich in blood cells and specifically in white cells such as monocytes, in particular a composition derived from blood such as that obtained by apheresis, said procedure includes the following stages:

advantageously a dilution of said composition derived from blood, particularly in approximately 2 to 3 times the volume of the latter, with the aid of an appropriate physiologic solution, a stage of washing said composition derived from blood, advantageously by simple centrifugation, and washing the pellet issued from the said centrifugation, after recovery of the pellet in an appropriate physiologic washing solution, particularly in a bag (a transfer type bag), effected, for example, by pressure on said bag, thus eliminating the washing solution to another bag or other recipient, to recover a composition depleted of possible anticoagulants, various residues and platelets, optionally, the repetition of the washing stage mentioned above, particularly from 1 to 2 times, a culture stage of the cells contained in the composition derived from blood obtained after the washing stage mentioned above, by placing said cells in an appropriate culture medium, in particular in a bag, advantageously hydrophobic, for about 6 to 7 days. This culture stage is optionally done in the presence of specific antigens mentioned above, that is, in particular, in the presence of antigens characteristic of tumor cells or of pathogens in the case of MD-APC production, and possibly followed by an activation stage of the macrophages or MD-APCs obtained in the culture medium, by addition in said culture medium of an activator such as interferon γ, said activator being placed in contact with the contents of the culture medium for about 16 to 24 hours. This stage of culture, and optionally activation, are possibly followed by centrifugation, in particular following the procedure indicated above, this stage of culture, and optionally activation, being:

preceded by a stage of elimination of all or part of the constituents other than the monocytes or their precursors, in particular the platelets, red cells, granulocytes, and lymphocytes, liable to be present in the starting composition, by contacting the composition derived from the blood obtained after the stage of washing preceding the stage of culture, with antibodies directed against all or part of the above mentioned constituents, and recovering the solution containing the monocytes or their precursors, all or part of the above mentioned constituents remaining fixed to the antibodies;

and/or followed by a stage of elimination of all or part of the constituents other than the macrophages or MD-APCs by being placed in contact with the composition derived from blood obtained after the culture stage with the antibodies such as described above, and recovery of the solution containing the macrophages or MD-APCs, all or part of the above mentioned constituents remaining fixed to the antibodies, and/or followed by a purification stage, in particular an elutriation, in which the macrophages or MD-APCs, optionally activated, are separated from the other constituents of the composition obtained after the stage of culture, and possibly the stage of activation mentioned above, separated from, in particular, the platelets, red cells and lymphocytes, by physical means.

The invention results from the discovery made by the inventors which shows that, contrary to ideas known in the field, it is possible to bring the culture of monocytes or their precursors into macrophages or MD-APCS to completion with good results when the culture medium contains controlled quantities of red cells, lymphocytes, granulocytes, and platelets.

The invention thus offers the advantage of having access to a process for obtaining macrophages or MD-APCs which enables to get rid of the stage of separation by physical means of, in one part, the mononucleated cells, and more specifically the monocytes, and, in another part, the red cells, granulocytes (and the vast majority if not the totality of platelets) contained in the composition derived from the blood obtained by apheresis, said stage being costly (requiring sophisticated material) and time consuming.

Advantageously, in the above mentioned process of the invention, the starting composition derived from the blood of human origin, namely the composition of cellular suspension enriched in blood cells, such as that issued from apheresis and before the stage of washing preceding the stage of culture in the procedure described above, is such that it includes a proportion of monocytes greater than about 5%, in particular about 10% to 30%, in number of white cells present in said composition.

Such a starting composition is advantageously obtained by the reduction to practice of process of apheresis conducted on a patient, this process being in particular carried out according to any technique and with any material known by any individual skilled in the art, optionally according to a process adapted for obtaining a starting composition such as defined here above and hereafter.

Advantageously, the starting composition derived from blood of human origin mentioned above can contain up to about 3% red cells, and preferably is such that it comprises a proportion of red cells less than about 1%, in particular from 0.3% to 0.5%, in number of white cells present in said composition.

Advantageously, the original composition derived from blood of human origin mentioned above is such that:

the number of platelets is between about $2 \times 10^{11}$ to about $6 \times 10^{11}$ in a volume of about 150 ml to about 200 ml, the number of white cells is between about $5 \times 10^9$ to about $5 \times 10^{10}$ in a volume of about 150 to about 200 ml, the proportion of lymphocytes is between about 60% to about 80%, in number of white cells present in the said composition, the proportion of monocytes is between about 10% to about 30%, in number of white cells present in said composition, the proportion of granulocytes is between about 10% to about 20%, in number of white cells present in said composition.

The stage of washing the starting composition, preferably repeated 2 times, permits the essential elimination of a part of the platelets, and optionally of the reagents used during the process of obtaining the original composition, in particular those of apheresis, such as anticoagulants. Advantageously, the percentage of platelets eliminated during this stage is about 80% to about 90%.

The composition obtained after the stage of washing the original composition contains advantageously, in a volume of about 600 ml, the following constituents:

| | |
|---|---|
| Hematocrit: | 0.2% to 0.4% in number of white cells present in said composition |
| Platelets: | about 2 to about $6 \times 10^{10}$ |
| White cells: | about $4 \times 10^9$ to about $4 \times 10^{10}$ |
| Lymphocytes: | about 60 to about 80% in number of white cells present in said composition |
| Monocytes: | about 10% to about 20% in number of white cells present in said composition |
| Polynuclear cells: | about 10 to about 15% in number of white cells present in said composition. |

According to a preferred embodiment of the process of the invention, the stage of culture and differentiation of the monocytes or their precursors into macrophages or MD-APCs is carried out from a composition derived from blood of human origin containing mononucleated cells, namely monocytes or their precursors and lymphocytes, as well as red cells (in appropriate quantities, in particular in the proportions indicated above), granulocytes and platelets, said culture stage being carried out in particular starting from the composition obtained after the stage of washing the starting composition, such as is described above.

Concerning the stage of culture itself, it preferably takes place over a period of about 6 to about 8 days in a specific ready to use culture medium based on modified IMDM (Iscove Modified Dubeleco Medium, Gibco), namely the Dubelcco medium modified by Iscove (IMDM) to which is added L-Glutamine (2 mM, Gibco) or advantageously L-Alanyl-L-Glutamine (2 mM, Gibco), pyruvic acid (2 mM, Gibco), Indomethacine ($5 \times 10^{-6}$ M, Sigma), mercaptoethanol ($3 \times 10^{-5}$ M, Gibco), and non-essential amino acids (2%, Gibco). At the time of culture, the medium will be supplemented by 2 to 5% AB$^+$ serum (or by autologous serum) as well as with antibiotics such as penicillin and streptomycin.

The invention more specifically relates to the above mentioned ready to use culture medium, containing L-Alanyl-L-Glutamine instead of L-Glutamine. The inventors have in fact shown evidence that the above mentioned ready to use culture medium containing L-Alanyl-L-Glutamine can advantageously be conserved at 4° C. with the group of constituents of the kits of the invention described hereafter, while the above mentioned ready to use culture medium containing L-Glutamine must be conserved at −20° C.

For the differentiation of monocytes into macrophages, the above mentioned culture medium is advantageously supplemented by GMCSF and vitamin D3.

For the differentiation of monocytes or their precursors into MD-APCs, the above mentioned culture medium is used for co-culture with the antigens described above, and is advantageously supplemented by one or many cytokines such as GMCSF, TNF-α, IL-13, IL-4, and/or by other adjuvants such as calcitriol and histamine.

In the case of obtaining activated macrophages or MD-APCs, an activator, such as interferon γ, is advantageously introduced in the above mentioned culture medium about 16 to about 24 hours before the end of the culture.

According to a preferred embodiment of the procedure described above, the composition of the cellular suspension obtained after the culture stage, in a volume of about 600 ml to 2000 ml, is advantageously the following:

Lymphocytes: about $2 \times 10^9$ to about $2 \times 10^{10}$

Macrophages (or MD-APCs): about $6 \times 10^8$ to about $6 \times 10^9$

This final composition includes little or no granulocytes, these having for the most part decomposed during the stage of culture.

The yields of the culture stage mentioned above are advantageously about 80% mononucleated cells, and about 50% to about 70% for the differentiation into macrophages or MD-APCs (taking into account the number of starting monocytes).

The above mentioned yields are calculated as the ratio between the number of macrophages or MD-APCs obtained after the culture stage and the number of monocytes present in the composition before culture.

Advantageously, in the preferred embodiment of the process of the invention described above, the above mentioned stage of culture, and optionally activation, is followed by a stage of purification, in particular by elutriation, in which the macrophages or MD-APCs, optionally activated, are separated from the other constituents of the composition obtained after the stage of culture, and optional activation mentioned above, separated in particular from the platelets, red cells and lymphocytes, by physical means.

Advantageously, the stage of culture, and optional activation, carried out in the preferred process mentioned above, is followed by a stage of elutriation represented in FIG. 3, this being preferably carried out using the following mechanism:

a bag (designated B4 in FIG. 3) containing the composition comprising macrophages or MD-APCs, optionally activated, obtained after the stage of culture, and after optional activation, as well as a bag containing a physiologic solution (also designated as elutriation solution) able to contain the entire elutriation system in a medium viable for the macrophages or MD-APCs, optionally activated, and an air intake are linked to a transfuser with three branches equipped with a filter, once the air intake is closed, a peristaltic pump pulls the contents of the bag B4 into an elutriator equipped with a rotor with an elutriation chamber, the feeding of the entirety of the elutriation circuit with physiologic liquid being assured by the pulling of the contents of the bag containing the elutriation solution, with the above mentioned pump, during the entire duration of the elutriation, the speed of rotation of the elutriation rotor and the delivery from the pump are such that the various constituents of the composition of bag B4, entering the rotor, are separated as a function of their size in the elutriation chamber; the constituents of the smallest size migrate firstly to the top of the chamber (near the exit of the elutriator), while the constituents of the largest size, namely the macrophages or MD-APCs, optionally activated, migrate to the exit of the chamber lastly, the different constituents of the composition in bag B4 thus separated are harvested separately into bags linked to the elutriator; the platelets and various residues of small size are recovered first into bag C1; the red cells are then recovered into bag C2, the lymphocytes into bags C3 and C4, and finally the macrophages or MD-APCs into bag E1, the different categories of constituents mentioned above being extracted from the elutriator as a function of their respective size, either by diminishing the speed of rotation of the elutriator, or by augmenting the delivery of the pump. The recovery of macrophages or MD-APCs into bag E1 is advantageously able to be carried out by stopping the rotor of the elutriator and opening the air intake; bag E1 thus contains the composition of macrophages or MD-APCs, optionally activated, advantageously in an essentially pure form.

As a variation of the preferred process described above, the culture stage and differentiation of monocytes or their precursors into macrophages or MD-APCs may be preceded by a stage of elimination of all or part of the constituents other than the mononucleated cells, specifically those other than the monocytes liable to be contained in the composition obtained after the stage of washing the original composition, such as is described above, said elimination stage being not carried out by physical means, but by carrying out immunological reactions between all or part of the above mentioned constituents and antibodies able to recognize said constituents.

The stage of elimination by antibodies mentioned above is advantageously carried out by contacting the composition issued from the stage of washing the starting composition with anti-platelet antibodies, and/or anti-red cell antibodies, and/or anti-granulocyte antibodies, fixed on a solid support, in particular on the walls of a transfer type bag, or on the walls of any other device in which said composition issued from the initial stage of washing is able to be introduced, said device being optionally set up in order to allow the circulation of said composition along the walls on which said antibodies are fixed.

Contacting said composition with said antibodies is carried out either simultaneously with all or part of the antibodies mentioned above, or successively in particular by introduction of said composition into a bag or other device such as is described above containing anti-platelet antibodies, then passing said composition into a second bag containing anti-red cell antibodies, and/or passing said composition into a third bag containing anti-granulocyte antibodies, the lymphocytes being eliminated during the stage of elutriation following the stage of culture.

According to another preferred embodiment of the process of the invention which specifically does not include a stage of elutriation, the included stage of culture, and optional activation, is:

preceded by a stage of contacting the composition issued from the stage of washing the starting composition with the anti-platelet antibodies, and/or anti-red cell antibodies and/or anti-granulocyte antibodies, fixed on a solid support, in particular in the manner indicated above, contacting said composition with said antibodies being carried out, either simultaneously with all or part of the above mentioned antibodies, or successively in particular in the manner indicated above, said composition being then transferred into a bag containing the culture medium, and followed by a stage of contacting the composition issued from said stage of culture, and optional activation, with the anti-lymphocyte antibodies, by introduction of said composition into one (or several) bag(s) or other device such as described above, containing anti-lymphocyte antibodies, and recovery the composition of macrophages or MD-APCs, optionally activated, being sought, in an essentially pure form.

Advantageously, when the preferred process above described is carried out by contacting the composition issued from the stage of washing the starting composition in successive contact with anti-red cell antibodies, then anti-platelet antibodies, then anti-granulocyte antibodies, the composition of the cellular suspension thus obtained before the stage of culture, in a volume of about 600 ml to about 2000 ml, is advantageously the following:

| | |
|---|---|
| Red cells: | <0.1% |
| Platelets: | <$10^{10}$ |
| White cells: | about $3 \times 10^9$ to about $3 \times 10^{10}$ |
| Lymphocytes: | about 60% to about 80% in number of white cells present in said composition |
| Monocytes: | about 20% to about 30% in number of white cells present in said composition |
| Polynuclear cells: | <5%. |

In the preferred process described above, the composition of the cellular suspension obtained after the culture stage, in a volume of about 600 ml to 2000 ml, is advantageously identical to that of the cellular suspension obtained after the culture stage in the preceding preferred procedure, not requiring a stage of immunological reaction previous to the culture stage, namely, Lymphocytes: about $2 \times 10^9$ to about $2 \times 10^{10}$ Macrophages: about $6 \times 10^8$ to about $6 \times 10^9$ The yields of the culture stage mentioned above are advantageously identical to those described in the preceding preferred procedure, namely about 80% mononucleated cells, and about 50% to about 70% for the differentiation into macrophages (taking into account the starting number of monocytes).

The yields of the processes described above are advantageously of the same order, be these processes carried out according to the principle of elutriation after the culture stage, or according to the principle of the immunological reaction before and after the culture stage.

Thus, the above described processes of the invention are such that one can obtain cellular suspensions comprising macrophages or MD-APCs, optionally activated, in an essentially pure form, in particular in proportions of about 80% to about 95%, and with final yields of about 20% to about 50% (said yields being calculated as a ratio between the quantity of purified macrophages or MD-APCs obtained at the end and the quantity of monocytes initially placed in culture).

According to a specifically advantageous embodiment of the processes of the invention described above, the composition of the starting cellular suspension, and/or at least one of the compositions of cellular suspension obtained under the different stages of the above mentioned procedures, and/or the composition of the final cellular suspension, is/are able to be compared to the compositions called internal controls, in order to make a good follow up of the processes of the invention.

An internal control particularly advantageous is that which is constituted of a determined quantity of monocytes, purified from blood taken from a healthy individual, advantageously fixed, in particular by lyophilization, said internal control allowing for the quantification of the number of monocytes present in the starting composition.

An internal control specifically preferred is that which includes about $2 \times 10^6$ to about $4 \times 10^6$ lyophilized monocytes in a volume of about 1 ml to about 2 ml of an aqueous solution.

The quantification of the number of monocytes present in the original composition is advantageously carried out by withdrawing an aliquot part of the starting composition, labelling the monocytes liable to be present in the fraction withdrawn, in particular with the aid of labelled antibodies, for example by radioactivity, enzymes, or by fluoresceine, revealing the labelling carried out by using any appropriate device, and comparing the intensity of the labelling obtained under the same operating conditions with said internal control.

The labelled antibodies able to recognize specific surface antigens of monocytes are advantageously those directed against, for example, the following antigens: CD14, HLADR, and CD64.

Another internal control specifically advantageous is that constituted from a determined quantity of macrophages or purified MD-APCs, optionally activated, from blood withdrawn from a healthy individual, advantageously fixed, in particular by lyophilization, then reconstituted in an adequate solution of 1 to 2 ml, said internal control allowing for the quantification of the number of macrophages or MD-APCs, optionally activated, present in the final composition.

An internal control specifically preferred is such that it includes about $2 \times 10^6$ to about $4 \times 10^6$ lyophilized macrophages in a volume of about 1 ml to about 2 ml of an aqueous solution.

The quantification of the number of macrophages present in the original composition is advantageously carried out by withdrawing an aliquot part of the original composition, labelling the monocytes present in the fraction withdrawn, in particular with the aid of labelled antibodies, for example by radioactivity, enzymes, or by fluoresceine, revealing the effected labelling by using any appropriate device, and comparing the intensity of the labelling obtained under the same operating conditions with said internal control.

The labelled antibodies able to recognize specific surface antigens of macrophages and/or MD-APCs are advantageously directed against at least one of the following antigens: CD54, CD58, CD80, CD86, CD14, CD16, MAX-1, CD64, HLADR described in particular in the following articles: Andreesen et al., Biology 47: 490–497 (1990), Lopez et al., Journal of Immunotherapy 11: 209–217 (1992), Chokri et al., Anticancer Research 12: 2257–2260 (1992).

Advantageously, the internal controls mentioned above are constituted from beads, chosen in particular from among fluorescent beads, having a diameter comparable to that of monocytes or macrophages, and able to give signals identical to those given by monocytes and macrophages in, respectively, the starting and final solutions.

According to another specifically advantageous embodiment of the processes of the invention described above, the control of the compositions of macrophages or MD-APCs, optionally activated; obtained when reducing to practice these processes, can be carried out by detection, and optionally measure of cytokines secreted by the macrophages in said compositions, and compared to the standard secretion profile of cytokines by macrophages or MD-APCs, optionally activated.

As an illustration, the detection of secreted cytokines such as IL-1 (Interleukin 1) and TNF-α (Tumor Necrosis Factor-α) can be carried out by withdrawing an aliquot part of culture medium in which the differentiation and the activation of macrophages obtained has taken place.

The macrophages and M-APCs, optionally activated, obtained by the process of the invention, may be tested for their capacity to recognize and kill tumor cells (in particular by cytotoxicity test) or, in the case of MD-APCs, for their capacity for antigenic presentation, in particular by verifying their capacity to induce allogenic lymphoproliferation (for example the MLR test, Mixed Lymphocyte Reaction). These tests allow to determine the number of functional units of macrophages or MD-APCs obtained during the process of the invention.

The invention also relates to kits (or cases) for obtaining compositions of macrophages or MD-APCs, optionally activated, characterized in that they comprise:

the necessary elements for washing, culture, and elutriation, including:
  one or several washing bag(s),
  one or several culture bag(s), preferably hydrophobic,
  one or several connector(s) and needle(s) for the elimination of the supernatant of the washings,
  one or several connection tube(s) between the preceding bags,
  optionally, one or several injection site(s) in the washing and culture bag(s),
  one or several systems allowing for the opening or the closing of the links between the washing bag(s) and the culture bag(s), in particular, systems of clamps on the tubes,
  two bags containing the physiologic solution for the washing and the elutriation,
  a three branch transfuser with air intake,
  a silicon tube and a joint on the rotor serving as a connection between the transfuser and the rotor of the elutriator,
  one (or several) collection bag(s), optionally linked together by tubes equipped with a clamp system,
  a tube and joint on the rotor serving as a connection between the collection bag(s) mentioned above and the rotor of the elutriator, the reactive agents necessary for the culture, differentiation, activation, and control, including:
  a bag of specific, ready to use culture medium, in particular at primarily constituted from modified IMDM, namely Iscove modified Dubelcco medium (IMDM, Gibco), to which has been added L-Glutamine (2 mM, Gibco) or L-Alanyl-L-Glutamine (2 mM, Gibco), pyruvic acid (2 mM, Gibco), Indomethacine ($5 \times 10^{-6}$ M, Sigma), mercaptoethanol ($3 \times 10^{-5}$ M, Gibco), non-essential amino acids (2%, Gibco), and 2 to 5% of AB$^+$ serum (or autologous serum), as well as antibiotics such as penicillin and streptomycin, added at the moment of culture, one or several supplements advantageously under liquid or lyophilized form, to be added to the culture medium, chosen from among the following:
GMSCF,
vitamin D3,
interleukin-13 (IL-13)
IL-4
TNF-α
histamine optionally, an activator such as interferon γ, advantageously under liquid or lyophilized form, advantageously one (or several) internal control(s) comprising monocytes, and/or macrophages or MD-APCs, the latter being optionally activated, advantageously fixed, or lyophilized, and optionally labelled, or calibrated beads, optionally labelled, in particular by fluorescence, one or several labelled antibodies, in particular by fluorescence, such as those directed against antigens CD3 marker for lymphocytes used in case of negative control), CD45 marker for leukocytes in general), CD14, CD16, CD64, CD54, CD58, CD80, CD86, HLA-DR and MAX-1.

A kit specifically advantageous in the framework of the present invention is presented in the form of two groups:
group I contains the bags, tubes, injection sites, clamp systems, and three branch transfuser, namely, the "dry" elements used for washing, culture, and the purification by elutriation,
group II contains a bag containing the specific culture medium as well as the reactive agents for the culture, differentiation, activation, and quality control.

The kit mentioned above is moreover characterized in that:
group I is constituted of two sub-groups in the form of two boxes:
box A containing the material necessary for washing the cells obtained from apheresis, in particular:
three bags with a capacity of 600 ml (central bag A1, and recovery bags A2 and A3 shown in FIG. 1),
a transfer set for transferring the washing solution into the bag (bag A1 in FIG. 1) in which is transferred the blood composition in order to dilute and wash the cells issued from apheresis,
a transfer set for the washed cells (contained in bag A1 in FIG. 1) to the culture bags (bags B1, B2, and B3 in FIG. 2),
a transfer set for the culture medium, firstly towards the washed cells (contained in bag A1 in FIG. 1), and secondly towards the culture bags mentioned above,
three hydrophobic culture bags with a capacity of 3 litres (bags B1, B2, and B3 in FIG. 2),
box B contains the elements for the separation of the differentiated macrophages or MD-APCs from the other cells present in the culture during the stage of elutriation, in particular:
a gathering bag (or pooling bag B4 in FIG. 2),
a three branch transfuser with air intake,
a silicon tube, two joints to the rotor, the tube and one of the two joints serving as a connection between the transfuser and the rotor of the elutriator, the other joint serving as a connection with said rotor and the group of bags mentioned hereafter, the latter tube containing a site for sample withdrawal,
a combination of four recovery bags (bags C1, C2, C3, and C4 in FIG. 3) with a capacity of one litre, a bag (bag E1 in FIG. 3) with a capacity of 600 ml to contain the final fraction of purified macrophages or MD-APCs, and a bag (bag E2 in FIG. 3) with a capacity of 600 ml for the recovery of the supernatant of the preceding bag, and a bag (bag E3 in FIG. 3) for injecting the patients with macrophages or MD-APCs, optionally activated, group II is represented by box C, an isothermal box, optionally with a cooling system to maintain the temperature at 4° C., and containing in particular:
a bag of 2 litres of culture medium primarily constituted from modified IMDM, as described above,
a box containing the following liquid or lyophilized products:
a flask of antibiotics (penicillin, advantageously 1,000 U/streptomycin, advantageously 1,000 μg),
a flask of vitamin D3 (advantageously 4 to 8 μg),
a flask of GMSCF (advantageously $5 \times 10^5$ to $10^6$ U),
a flask of interferon γ (advantageously $25 \times 10^4$ to $5 \times 10^5$ U),
a flask of IL-13,
a flask of IL-4,
a flask of TNFα,
a flask of histamine,
a box containing one (or several) internal control(s) as described above, and one or many flasks containing the labelled antibodies anti-CD3, anti-CD45, anti-CD14, anti-CD16, anti-CD64, anti-MAX-1, anti-CD54, anti-CD58, anti-CD80, anti-CD86, and anti-HLA-DR, in particular labelled with fluoresceine.

The invention also refers to the use of a kit as defined above for the realization of a process as described above according to the invention including a stage of elutriation.

The invention also relates to a kit for obtaining compositions of macrophages or MD-APCs, optionally activated, characterized in that it includes:
one (or several) bag(s) inside of which fixed anti-red cell antibodies are found,
one (or several) bag(s) inside of which fixed anti-platelet antibodies are found,
one (or several) bag(s) inside of which fixed anti-granulocyte antibodies are found,
one (or several) bag(s) inside of which fixed anti-lymphocyte antibodies are found,
one (or several) culture bag(s),
one (or several) bag(s) for the recovery of purified macrophages or MD-APCs, optionally activated,
linking tubes between the different bags mentioned above,
supplements advantageously under liquid or lyophilized form, to be added to the culture medium, in particular:
antibiotics such as penicillin and streptomycin,
GMCSF,
vitamin D3,
IL-13
IL-4
TNFα
histamine
optionally, an activator such as interferon γ, advantageously under liquid or lyophilized form,
advantageously one (or several) internal control(s) comprising monocytes, or macrophages or MD-APCs, optionally activated, advantageously fixed, and optionally labelled, or of calibrated beads, optionally labelled, in particular by fluorescence, such as is described above, labelled antibodies, in particular by fluorescence, such as those directed against the antigens CD3, CD45, CD14, CD16, CD64, CD54, CD58, CD80, CD86, MAX-1 and HLA-DR.

The invention relates more specifically to the use of a kit as described above for carrying out a process as described above according to the invention comprising a stage of immunological reaction.

The invention also concerns any liquid composition containing a cellular suspension derived from blood of human origin, characterized in that it includes a proportion of monocytes greater than about 5%, in particular about 10% to about 30%, in number of white cells present in said composition.

The invention also relates to any composition such as described above, characterized in that it includes a proportion of red cells less than about 3% or less than about 1%, in particular from 0.3% to 0.5%, in number of while cells present in said composition.

The invention relates more specifically to any composition such as described above, characterized in that:

the number of platelets is between about $2 \times 10^{11}$ to about $6 \times 10^{11}$ in a volume of about 150 ml to about 200 ml, the number of white cells is between about $5 \times 10^9$ to about $5 \times 10^{10}$ in a volume of about 150 ml to about 200 ml, the proportion of lymphocytes is between about 60% to about 80%, in number of white cells present in the said composition, the proportion of granulocytes is between about 10% to about 20% in number of white cells present in said composition.

The invention refers more specifically to the above mentioned compositions such as obtained in the process of apheresis, carried out in particular on a volume of blood of approximately 5 to 10 litres.

The invention also relates to the use of a composition such as described above for obtaining a composition of macrophages or MD-APCs, optionally activated, in particular by carrying out a process according to the invention, said composition being able to be administered to a patient, optionally after dilution of the macrophages or MD-APCs, optionally activated, thus obtained in an appropriate injectable solution.

The invention also relates to the compositions (in particular pharmaceuticals or vaccines) containing macrophages and/or MD-APCs, optionally activated, in particularly in the proportions of purity indicated above, and such as are obtained by carrying out the process of the invention, optionally in association with an acceptable pharmaceutical vehicle.

The invention also relates to the compositions which can be used as internal controls in the framework of reducing to practice a process according to the invention, such as described above.

As an example, the internal control in the framework of the preparation of activated macrophages is presented in the following manner:

Contents:

1 flask of lyophilisate ($3 \times 10^6$/flask)

1 flask of reconstitution solution.

Reconstitution:

Rehydrate the flask of lyophilisate with 1 ml of the solution of reconstitution solution.

Mix gently by turning. Wait at least 10 minutes before using the preparation.

Use the volume of internal control used is 100 µl ($3 \times 10^5$ cells)

add the antibody to be tested incubate for 30 minutes at room temperature add 1 ml of PSB (do not wash)

analyze by cytofluorometry

The percentage and intensity of labelling of freshly prepared MAK or MD-APCs will be compared to the cells produced.

Table 1 which follows gives an indication of the evolution of membrane markers in relation to time of storage, of the lyophilized macrophages used as internal controls. The results are expressed as percentage of positive cells and intensity of labelling. The line "Ctrl" corresponds to the results obtained with fresh, non-lyophilized macrophages, cultivated and obtained according to the procedure of the invention. The line "7 Days" corresponds to macrophages obtained according to the process of the invention, lyophilized and rehydrated 7 months after lyophilization. An overall statement can be made that the percentages of positive cells as well as the intensities of labelling are kept equivalent to or similar to the fresh macrophages and those which are conserved in a lyophilized state for 7 days or 7 months. Thus, the user of the kits of the invention is able to compare the compositions which will be obtained with the internal controls (or standards) furnished with the kit, said controls being advantageously produced according to the same process and being lyophilized.

TABLE 1

| | Markers | | | | | |
|---|---|---|---|---|---|---|
| | CD45 | CD3 | CD14 | CD16 | CD64 | HLADR |
| Ctrl | 92/115 | 0.3/54 | 87/149 | 22/35 | 77/63 | 84/115 |
| 7 Days | 95/131 | 3/30 | 96/119 | 10/30 | 93/59 | 96/169 |
| 7 Months | 91/119 | 3/22 | 86/95 | 10/25 | 81/54 | 82/116 |

Advantageously, the kits of the intention are accompanied by written procedure forms for the preparation of macrophages or MD-APCs, optionally activated.

Advantageously, the kits of the invention are also accompanied by automated computerized instructions to guide the user through the processes and validate each step of the processes of the invention, the final goal being to determine the above mentioned number of functional units obtained by carrying out the processes of the invention.

As an illustration, the written procedure forms for the step of activating macrophages, accompanying a kit according to the invention, can be presented in the following manner:

MAK ® PREPARATION

Patient Code:                           Date:

- Attach bar code labels to each of the two tubes.
- Bacteriological Control J6
  Destination: _____
- Fill in the form "Bacteriological Control J6" which is in the MAK Liaison Documents" folder. Send the form and tubes to the control destination.
- Circle the word "ACTIVATION" on bags B1, B2 and B3.
- Put bags B1, B2 and B3 back in their initial location in the incubator (see page 9).

-continued

MAK ® PREPARATION

Patient Code:                              Date:

· Destroy any remaining gamma interferon.
    Date of destruction: _____
    Name: _____
    Signature: _____
· Complete below:

Signature of person responsible for this preparation:                              page x
· Remove bag B1 from the incubator and complete steps (1)
  through (4) under a flux laminar hood:
    Brand: _____
    Model no. _____
    (1) Withdraw volume $V_i$ of gamma interferon solution using
        a sterile, 1 ml syringe.
            Withdraw completed:   YES ☐
                                  NO ☐
    (2) Inoculate the solution of gamma interferon into the bag.
    (3) Without removing the syringe, aspirate and reinject its
        contents until homogenization.
    (4) Withdraw from the bag under sterile conditions and in one single
        withdrawal 1 ml to be distributed into two tubes as follows:
        · 0.5 ml of cellular suspension for cell count, viability, and
          size control (see appendix No.7 (A), page 33).
        · 0.5 ml of cellular suspension for bacterial control (see
          appendix No. 7 (D), page 35).
· Remove bag B2 from the incubator and repeat steps (1) through (4).
  Add 0.5 ml to each of the two tubes already used for the
  controls for bag B1.
· Remove bag B3 from the incubator and repeat steps (1) through (4).
  Add 0.5 ml to each of the two tubes already used for the
  controls for bags B1 and B2.
    Samples taken:
    Bag 1:   YES ☐   Bag 2:   YES ☐   Bag 3:   YES ☐
             NO  ☐            NO  ☐            NO  ☐
Signature of person responsible for this preparation:                              page x Description of the figures The description of the operations represented by FIGS. 1 through 3 is as follows:

I-REMOVAL OF PLATELET FROM THE PRODUCT OF APHERESIS (FIG. 1)

(1) Transfer the contents of the apheresis bag into bag A1 (600 ml capacity).

(2) To the bag containing the mononucleated cells, add a weight of buffered saline solution such that the final weight of the bag is 450–500 g.

(3) Centrifuge bag A1 at 300 g for 10 minutes at +4° C.

(4) Transfer the supernatant into bag A2, using a press.

(5) Fill to 450 g with saline solution.

(6) Centrifuge bag A1 a second time.

(7) Transfer the supernatant into bag A3.

Detach the cells from the centrifugation bag A1 by friction.

(8) Fill to 600 ml with culture medium which has been previously prepared.

Note the volume of culture medium added.

Withdraw the control samples under sterile conditions.

II-CULTURE OF MONONUCLEATED CELLS (FIG. 2)

(9) Distribute equally into the culture bags B1, B2 and B3.

(10) Fill the volume required for each bag with culture medium.

(11) At the end of the culture and activation periods, transfer the contents of the three culture bags into the pooling bag B4.

III-SEPARATION BY ELUTRIATION (FIG. 3)

Attach part I (entry of Kit) to the entry of the sterilized elutriation chamber and the exit of the kit (part II) to the exit of the elutriation chamber

(12) Fill the circuit with at least 300 ml of elutriation solution.

(13) Simultaneously, close the entryway of the elutriation solution and open that of the cellular suspension bag (bag B4) without changing the delivery of the pump.

As soon as all of the cells have passed, close the entryway of the bag B4 of cells and open that of the elutriation solution.

Increase the delivery of the pump every 500 ml and withdraw a sample.

(14) When cells having the size of macrophages begin to exit, stop the centrifugation and deviated the withdrawal to the collection bag E1 by closing the entryway of the elutriation solution and opening the air intake.

(15) Centrifuge bag E1 at 400 g for 10 min.

(16) Transfer the supernatant into bag E2.

(17) Put the cells back into suspension in a solution of 250 ml of human albumin at 4%. Homogenize well.

(18) Transfer into the injection bag E3.

What is claimed is:

1. A kit for obtaining compositions of macrophages, or MD-APCs, comprising:
   necessary elements for washings, culture and elutriation, including:
      at least one bag for washing,
      at least one culture bag,
      at least one connector for eliminating supernatant from the washings,
      at least one connecting tube between the preceding bags,
      at least one injection site in the washing and culture bags,
      at least one system allowing for opening and closing of the at least one connecting tube between the at least one washing bag and the at least one culture bag,
      two bags containing a physiologic solution for the washings and the elutriation,
      a three branch transfuser with air intake,
      a silicon tube and a joint on a rotor serving as a connection between the transfuser and the rotor of the elutriator,
      at least one collection bag,
      a tube and a joint on the rotor serving as a connection between the at least one collection bag and the rotor of the elutriator,
   necessary reactive agents for the culture, differentiation, activation and control, including:
      a bag of specific, ready to use culture medium, to which has been added L-Glutamine (2 mM, Gibco) or L-Alanyl-L-Glutamine (2 Mm, Gibco), pyruvic acid (2 mM, Gibco), Indomethacine ($5 \times 10^{-6}$ M, Sigma), mercaptoethanol ($3 \times 10^{-5}$ M, Gibco), non-essential amino acids (2%, Gibco); 2 to 5% of one of $AB^+$ serum and autologous serum,
      at least one supplement to be added to the culture medium, selected from a group consisting of:
         GMSCF,
         vitamin D3,
         interleukin-13 (IL-13)
         IL-4
         TNF-α
         histamine
      at least one internal control comprising at least one of monocytes, and macrophages or MD-APCs, at least one labelled antibody.

2. A kit according to claim 1, wherein the kit is presented in two groups:
   group I containing the bags, tubes, injection sites, opening and closing systems, and three branch transfuser,
   group II containing a bag containing the specific culture medium as well as reactive agents for the culture, differentiation, activation and quality control.

3. A kit according to claim 2, wherein:
   group I consists of two sub-groups in the form of two boxes:
      box A comprising cell washing material, including:
         a transfer set for transferring the washing solution into the central bag A1 in which is transferred the blood composition in order to dilute and wash the cells issued from apheresis,
         a transfer set for transferring the washed cells from the central bag A1 to the culture bags,
         a transfer set for transferring the culture medium, to the central bag A1, and to the culture bags,
         three hydrophobic culture bags, each having a capacity of 3 litres,
      box B containing elements for the separation of the differentiated macrophages or MD-APCs from other cells present in the culture during the stage of elutriation, including:
         a gathering bag,
         a three branch transfuser with air intake,
         a silicon tube, two joints to the rotor, the tube and one of the two joints serving as a connection between the transfuser and the rotor of the elutriator, the other joint serving as a connection with said rotor and the group of bags mentioned hereafter, the latter tube containing a site for sample withdrawal,
         a combination of four recovery bags with a capacity of one litre, a bag with a capacity of 600 ml to contain the final fraction of purified macrophages or MD-APCs, and a bag with a capacity of 600 ml for the recovery of a supernatant of the final fraction bag, and a bag for injecting the patients with macrophages or MD-APCs,,
   group II contains an isothermal box C, containing:
      a 2 litre bag of culture medium primarily constituted from modified IMDM,
      a box containing the following liquid or lyophilized products:
         a flask of antibiotics,
         a flask containing 4 to 8 $\mu$g of vitamin D3,
         a flask containing $5 \times 10^5$ to $10^6$ U of GMSCF,
         a flask containing $25 \times 10^4$ to $5 \times 10^5$ U of interferon $\gamma$,
         a flask of IL-13,
         a flask of IL-4,
         a flask of TNF$\alpha$,
         a flask of histamine,
      a box containing at least one of the internal controls, and flasks containing the labelled antibodies anti-CD3, anti-CD45, anti-CD14, anti-CD16, anti-CD64, anti-MAX-1, anti-CD54, anti-CD58, anti-CD80, anti-CD86, and anti-HLA-DR, labelled with fluoresceine.

4. The kit of claim 1, wherein the at least one culture bag is hydrophobic.

5. The kit of claim 1, wherein the system allowing for opening and closing of the at least one connecting tube comprises clamps.

6. The kit of claim 1, wherein there are a plurality of the collection bags, the collection bags being linked to one another by tubes equipped with clamps.

7. The kit of claim 1, wherein the culture medium comprises modified IMDM.

8. The kit of claim 1, wherein the antibiotics added to the culture medium include at least one of penicillin and streptomycin.

9. The kit of claim 1, wherein the at least one supplement is in one of liquid and lyophilized form.

10. The kit of claim 1, further comprising interferon $\gamma$ as an activator, in one of liquid and lyophilized form.

11. The kit of claim 1, wherein the at least one internal control includes fixed and activated macrophages or MD-APCs.

12. The kit of claim 11, wherein the at least one internal control includes calibrated beads labeled by fluorescence.

13. The kit of claim 1, wherein the at least one labeled antibody is labeled by fluorescence.

14. The kit of claim 3, wherein the isothermal box comprises a cooling system capable of maintaining a temperature of 4° C.

15. The kit of claim 3, wherein the flask of antibiotics includes at least one of penicillin and streptomycin.

16. A kit for obtaining compositions of macrophages or MD-APCs, including:
   at least one bag containing fixed anti-red cell antibodies,
   at least one bag containing fixed anti-platelet antibodies,
   at least one bag containing fixed anti-granulocyte antibodies,
   at least one bag containing fixed anti-lymphocyte antibodies,
   at least one bag culture bag,
   at least one bag for recovery of purified macrophages or MD-APCs,
   tubes for joining the bags,
   supplements to be added to a culture medium, including:
      antibiotics,
      GMSCF,
      Vitamin D3
      IL-13,
      IL-4,
      TNF-$\alpha$,
      histamine,
   marked antibodies.

17. The kit of claim 16, wherein the supplements are in one of a liquid and lyophilized form.

18. The kit of claim 16, further comprising interferon $\gamma$ as an activator in one of liquid and lyophilized form.

19. The kit of claim 18, further comprising at least one internal control comprising at least one of monocytes and macrophages or MD-APCs.

20. The kit of claim 19, further comprising calibrated beads.

21. The kit of claim 16, wherein the marked antibodies are marked by fluorescence.

* * * * *